United States Patent
Mayser

(10) Patent No.: US 8,765,712 B2
(45) Date of Patent: Jul. 1, 2014

(54) AGENT FOR PREVENTING AND TREATING PITYRIASIS VERSICOLOR

(75) Inventor: Peter Mayser, Biebertal (DE)

(73) Assignee: Justus-Liebig-Universitaet Giessen, Giessen (DE)

( * ) Notice: Subject to any disclaimer, the term of this patent is extended or adjusted under 35 U.S.C. 154(b) by 167 days.

(21) Appl. No.: 13/144,613

(22) PCT Filed: Jan. 14, 2010

(86) PCT No.: PCT/EP2010/050397
§ 371 (c)(1),
(2), (4) Date: Dec. 12, 2011

(87) PCT Pub. No.: WO2010/081849
PCT Pub. Date: Jul. 22, 2010

(65) Prior Publication Data
US 2012/0129800 A1    May 24, 2012

(30) Foreign Application Priority Data

Jan. 14, 2009 (DE) .......... 10 2009 004 959
Jul. 29, 2009 (DE) .......... 10 2009 035 114

(51) Int. Cl.
*A61K 31/195* (2006.01)
*A61K 31/15* (2006.01)
*A61K 31/17* (2006.01)

(52) U.S. Cl.
CPC ............... *A61K 31/15* (2013.01); *A61K 31/17* (2013.01); *A61K 31/195* (2013.01)
USPC .............................. 514/50; 514/23; 514/263.3

(58) Field of Classification Search
CPC ....................................................... A61K 31/15
USPC .......................................................... 514/50
See application file for complete search history.

(56) References Cited

U.S. PATENT DOCUMENTS

2004/0235755 A1* 11/2004 Eigenbrodt et al. ............ 514/23
2008/0138417 A1   6/2008 Grigsby

FOREIGN PATENT DOCUMENTS

WO   WO-2005/016386 A1   2/2005
WO   WO-2007/054833      5/2007
WO   WO-2008/117079 A1  10/2008

OTHER PUBLICATIONS

Wills et al. Effect of mutants and inhibitors on mitochondrial transport systems in vivo in yeast. Biochim Biophys Acta 778:57-66, 1984.*
Glossary of medical education terms, Institute of International Medical Education. http://www.iime.org/glossary.htm Accessed in Mar. 2013.*
Gupta et al. Pityriasis versicolor: a review of pharmacological treatment options. Expert Opin Pharmacother 6:165-178, 2005.*
Examination Report for DE 10 2009 004 959 dated Sep. 30, 2009.
Inamadar, "The genus *Malassezia* and human disease," *Indian J. Dermatol. Leprol.*, 69(4):S265-270 (2003).
Database WPI Week 200873, Acession No. XP-002574533, S. Li, CN 101229234, Jul. 30, 2008.
International Search Report in corresponding PCT/EP2010/050397 dated Apr. 8, 2010.
Korsun et al., "Some Problems of the Pathogenesis and Therapy of Tinea Versicolor," Database Biosis Acession No. PREV197662049372 (1975).
Mayser et al., "Rapid reversal of hyperpigmentation in pityriasis versicolor upon short-term topical cycloserine application," *Mycoses* 52 (6): 541-543 (Nov. 2009).
Thoma et al., "Pityriasis versicolor alba," *Journal of the European Academy of Dermatology and Venereology* 19(2): 147-152 (Mar. 2005).
Zuther et al., "The tryptophan aminotransferase Tam1 catalyses the single biosynthetic step for tryptophan-dependent pigment synthesis in *Usitlago maydis*," *Molecular Microbiology* 68(1): 152-172 (Apr. 2008).

* cited by examiner

*Primary Examiner* — Brandon Fetterolf
*Assistant Examiner* — Yih-Horng Shiao
(74) *Attorney, Agent, or Firm* — Marshall, Gerstein & Borun LLP

(57) ABSTRACT

The present invention concerns an agent for prevention and treatment of pityriasis.
The agent according to the present invention comprises at least one transaminase inhibitor effectively inhibiting the transamination process which is of pathogenetic relevance for the disease, prevents a recurrence of the disease and which protects the human skin flora. Upon release into the environment, no resistances are induced in other fungi.

9 Claims, 2 Drawing Sheets

AGENT FOR PREVENTING AND TREATING PITYRIASIS VERSICOLOR

The present invention concerns the utilization of at least one transaminase inhibitor, in particular of aminooxyacetate and/or cycloserine and derivatives thereof, for the manufacture of an agent suitable for prevention and treatment of pityriasis (pityriasis versicolor).

DESCRIPTION OF THE GENERAL FIELD OF THE INVENTION

Pityriasis (pityriasis versicolor) is one of the most frequent fungal diseases in humans. The disease is caused by yeasts of the genus *Malassezia* (other name: *Pityrosporum ovale, orbiculare*), in particular also by *Malassezia furfur*. *Malassezia* yeasts belong to the normal skin flora of humans and many warm-blooded animals. In the case of a specific predisposition, often in combination with heavy perspiration, the fungus is however able to proliferate, to form hyphae and to cause pityriasis. This disease is characterized by scaly hyper- or hypopigmented lesions which exhibit only low inflammatory activity despite a high fungal load. Lesions show a characteristic yellow-greenish fluorescence which is used for diagnostic purposes. Furthermore, the disease is characterized by light to dark brown, partly erythematous macules which preferentially occur in those regions of the trunk which are rich in sebaceous glands. The infection sites are initially only lentilto penny-sized (approx. 1.5 cm) and tend to coalesce into map-like patterns. If a wooden spatula is scraped over these lesions, a fine bran-like (=pityriasiform) scaling becomes evident ("wood shavings phenomenon"). Frequently observed under UV-exposure, but also in unexposed areas of the skin, hyperpigmented areas change ("versicolor") into white, not or only slightly scaling lesions (pityriasis versicolor alba). Regimentation may require up to several month.

Apart from these often highly perturbing cosmetic aspects, patients are not impaired by this disease. Occasionally, a moderate itching sensation is described, particularly in case of increased perspiration. Primarily affected are adolescents and younger people in the second and third decade of life, while beyond age 60, the incidence is considerably lower. With the exception of tropical regions, the disease is rarely found in patients under the age of 10, since the change of skin lipid composition during puberty also plays an important role. No apparent gender preference exists. Noticeable however is the influence of the macroclimate. In tropical to subtropical regions, approximately every second person is affected by this disease. In Northern and Central Europe, pityriasis versicolor has an incidence of 0.5-1%, with a maximum in the months of May to September.

The contiguousness is generally considered to be low or non existent. Epidemic occurrence or partner infections were described only infrequently. In single cases, the disease could however be reproduced experimentally. In addition to a tropical, warm-humid macroclimate, also the individual tendency to perspire (e.g. associated with hyperthyreosis, tuberculosis, mailgrams) and the influence of the microclimate (occlusion) are among the predisposing factors, furthermore malnutrition, a positive family case history, and the use of lipid-containing external preparations. The unchanged incidence in patients who concomitantly suffer from coexisting diabetes mellitus or AIDS argues against a significant pathogenetic relevance of immune suppression.

In general, pityriasis versicolor is diagnosed clinically, supplemented by Wood's light examination (yellowish-green fluorescence) and KOH preparation. Microscopically, highly characteristic short, partly fragmented fungal hyphae in addition to round yeast cells ("spaghetti and meat balls") are found in the scales. Culturing the fungus (in lipid-containing media such as Dixon's or Leeming and Notman's agar) is not required, since the pathogen is a member of the resident flora of the human skin. *M. globosa* was however identified as dominant species in pityriasis lesions and, due to the round budding cells, suspected to be the pathogenic agent.

State of the Art

The disease can be treated, but strongly tends to take a recurrent course. General measures are among others to bathe/shower frequently using syndets, to avoid occlusive clothing, and to eliminate predisposing factors. Topically effective are antimycotics of the azole group, ciclopirox olamine and terbinafine, but also classical therapeutics such as sodium thiosulfate, zinc pyrithione, sulfur, propylene glycol and selenium disulfide. If applied topically, always the whole body should be treated, and shampoos or solutions containing the active agent are thus preferred. Systemic therapy is only indicated in the case of large infection sites or frequent recurrences. For this purpose, the azoles itraconazole and fluconazole are available.

Unfortunately, the disease may temporarily disappear as a result of a previous treatment, but cannot be cured, since always a few yeast cells remain on the skin which may then initiate a new disease process. In addition, particularly depigmented areas of the skin are, once they are formed, no longer accessible for a therapy with antimycotic agents.

The state of the art knows miscellaneous shampoos, ointments, gels and sprays for the treatment of pityriasis which contain antimycotics (e.g. ketoconazole, terbinafine) or selenium sulfide. Even though the disease is treated with these antimycotics, the tendency to recur is high and annoying after-effects occur if therapy is delayed. These agents require a daily treatment and at regular intervals, but are still not able to prevent a reappearance of the fungus and the symptoms. Hypopigmentation associated with the disease often persists for month. As homeopathic agents, potassium chloratum and potassium phosphoric are recommended.

To date, no agent is known by the state of the art which is able to treat pityriasis reliably and which is suitable for prevention.

Therefore, demand exists for an effective agent for the treatment and prophylaxis of pityriasis.

Despite the fact that the fungus is eliminated by antimycotics, the disease reappears frequently. Furthermore, if depigmentation has already occurred, even an antimycotic therapy does not cause healing. The utilization of antimycotics in particular for prevention is highly unsuitable since these substances are largely released into the environment and may consequently induce also resistances in other fungi. In addition, the use of antimycotics has a negative impact on the normal skin flora, since *Malassezia* yeasts also belong to the human resident flora.

Aim

Aim of the present invention is to eliminate disadvantages of the state of the art and to provide an effective agent for the treatment and prophylaxis of pityriasis, which prevents frequent recurrence of the disease and protects the human skin flora.

Solution of the Aim

The aim is solved by utilization of at least one transaminase inhibitor and an agent consisting of at least one transaminase inhibitor according to the claims. The transaminase inhibitor causes an inhibition of the transamination process which is an important pathogenetic factor for disease development, and is suitable for the treatment and prevention of pityriasis, thus preventing recurrence of the disease and preserving the human skin flora.

The agent according to the present invention has the advantages that it is well tolerated and particularly well suited for pityriasis prophylaxis. If applied in humans, the skin flora is protected, and no resistances are induced in other fungi if this agent is released into the environment.

The agent according to the present invention is furthermore particularly well suited for utilization in pityriasis therapy, since the metabolic pathway underlying this disease is specifically inhibited by at least one transaminase inhibitor of this invention.

Surprisingly it became evident that the disease-causing event in pityriasis is the synthesis of pigments and fluorochromes by *Malassezia* yeasts.

*M. furfur* is for example able to synthesize a variety of complex indole compounds if tryptophan is offered as sole nitrogen source. These indole compounds exhibit interesting biological features which account for the pathogenesis of pityriasis versicolor.

Malassezin, the first open chain aryl hydrocarbon receptor agonist (AhR), induces a dose-dependent apoptosis in human melanocytes, thus contributing to the depigmentation process. The UV-protective features of pityriacitrin explain why no increased UV sensitivity can be observed in depigmented areas. Pityriarubins A, B, and C are inhibitors of the respiratory burst of granulocytes which explains the low inflammatory activity in lesions despite a high fungal load. The fluorochrome pityrialactone might explain the fluorescence of skin lesions which is used diagnostically.

Further investigations with the closely related organism *Ustilago maydis* showed that the biosynthesis of this vast variety of complex indole derivatives from tryptophan requires only a single, enzymatically catalyzed step. This step, the deamination of tryptophan to indolepyruvate, is in *U. maydis* catalyzed by tryptophan aminotransferase TAM 1. A similar enzyme was also detected in *Malassezia* yeasts. Utilizing a tryptophan aminotransferase inhibitor, pigment synthesis in *M. furfur* is prevented. This clearly shows that TAM 1 of *M. furfur* is responsible for the tryptophan-dependent pigment synthesis.

Research results demonstrate that in the pathogenesis of pityriasis versicolor, tryptophan-dependent indole compounds synthesized by *Malassezia* yeasts are important which are induced under certain circumstances, namely the absence or depletion of other utilizable amino nitrogen compounds in the skin. These compounds are spontaneously formed from indolepyruvate after transamination of tryptophan to indolepyruvate, as well as in a reaction with residual tryptophan.

The biosynthesis of this vast variety of complex indole derivatives from tryptophan requires only a singe, enzymatically catalyzed step which is mediated by transaminase 1 (TAM 1).

Surprisingly it was observed that this tryptophan-dependent pathway important for pityriasis versicolor is completely inhibited if transaminase inhibitors such as e.g. the transaminase inhibitor aminooxyacetate [O-(carboxymethyl)hydroxylamine hemihydrochloride; chemical formula $C_2H_5NO_3 \cdot 1/2HCl$, molecular mass 109.29, CAS: 2921-14-4] are utilized.

An agar diffusion assay demonstrates that pigment synthesis is completely inhibited, while fungal growth is not impaired.

A comparable suppression of pigment formation in vitro and in vivo in humans is also achieved if transaminase inhibitors such as e.g. D-cycloserine (CAS: 68-41-7), DL-cycloserine (CAS: 68-39-3) or L-cycloserine (CAS: 339-72-0) are used. This also applies to the utilization of derivatives of D, DL or L-cycloserine like e.g. terizidone (CAS:25683-71-0) which also inhibit pigment formation and can therefore be utilized for prevention and therapy of pityriasis versicolor.

According to the present invention, a new approach for prevention and therapy of pityriasis versicolor is provided. This approach is not primarily aimed at antimycotic effects resulting in an elimination of the fungus, but rather at an inhibition of the transamination process which is an important pathogenetic factor for disease development. Herewith, the synthesis of tryptophan-dependent pigments which the disease is based upon and consequently disease manifestation itself is prevented. According to own results, pityriasis versicolor is based on a metabolic adaptation of the fungus to changing living conditions on the skin surface and represents no mycosis/infection in the narrow sense. After depletion of easily available nitrogen sources such as glycine, the amino group of tryptophan is transferred to phenylpyruvate by transamination. Indolepyruvate converted from TRP in this reaction reacts with itself and with tryptophan to those compounds which account for the pathogenesis of pityriasis versicolor.

More specific than the use of antimycotics is therefore the utilization of transaminase inhibitors, in particular a specific inhibitor for the inhibition of transaminase TAM 1.

According to the present invention, transaminase inhibitors, in particular the specific inhibitor for transaminase TAM 1, are used in topical application for the treatment and also prevention of pityriasis versicolor.

Particularly preferred, the transaminase inhibitor aminooxyacetate is used which exhibits in agar diffusion assays, either unbuffered or buffered (pH 5.0), efficacy in concentrations ranging from 0.05 to >0.5 molar.

Alternatively, also canaline and carboxymethoxylamine, cycloserines like D-cycloserine (CAS: 68-41-7), DL-cycloserine (CAS: 68-39-3) or L-cycloserine (CAS: 339-72-0), tunicamycin (CAS: 11089-65-9) or monoamine oxidase (MAO) inhibitors are used alone or in combination as transaminase inhibitors. Furthermore non-convertible substrate analogs of TAM 1 like for example nitrotryptophan, phenelzine (CAS: 156-51-4), 6-mercaptopurine monohydrate (CAS:6112-76-1), 6-thioguanine (CAS:154-42-7), D-galactosamine hydrochloride (CAS:1772-03-8) or 2-(hydroxyethyl)urea (CAS: 2078-71-9). Alternatively, as transaminase inhibitor, also cycloserine-derivatives such as terizidone (CAS:25683-71-0) are employed, alone or in combination with compounds chosen from the group of canaline (CAS: 39665-21-9), tunicamycin (CAS: 11089-65-9), GABA (CAS:56-12-2), hydrazine hydrochloride (CAS: 304-20-1), S(+)-γ-vigabatrin (CAS: 74046-07-4), gabaculine hydrochloride (CAS: 59556-17-1), isotonic acid (CAS:2552-55-8), γ-guanidino butyrate (CAS: 463-00-3).

TAM 1 is thereby inhibited in a competitive or non-competitive manner.

According to the present invention, the at least one transaminase inhibitor is applied topically, for example as shampoo, solution, lotion, cream, and ointment. Alternatively, transaminase inhibitors are utilized in combination with antipruritic agents, in particular with polidocanol (CAS: 3055-99-0).

Applied in concentrations between 5-10%, polidocanol exhibits in addition an antimycotic activity against *Malassezia* yeasts. Since the transamination of tryptophan is only induced when other metabolizable nitrogen sources are lacking in the skin environment, the embodiment also includes a combination of those nitrogen sources which are metabolizable by *Malassezia* yeasts. Urea for example belongs to the group of nitrogen sources which can be metabolized by *Malassezia* yeasts and which at the same time exhibits a conditioning and moisturizing effect on the skin.

Alternatively, the at least one transaminase inhibitor is used in combination with commonly known antimycotics. Furthermore, a combination is possible with other commonly used compounds well known to the expert in this field.

According to the present invention, the agent for treatment and prevention of pityriasis, in particular the specific inhibitor to inhibit transaminase TAM 1, is applied topically, for example as shampoo, solution, lotion, cream, ointment in combination with polidocanol or antimycotics or with other suitable compounds known by the expert.

In the following, exemplary embodiments of the present invention are described in more detail, whereby this invention is not restricted to said embodiments.

EMBODIMENTS

1. Induction of the Pigment Pathway

A specific feature of the nitrogen metabolism in *Malassezia* yeasts is the synthesis of pigments and fluorochromes if tryptophan (TRP) is offered as sole nitrogen source. This effect can in particular be induced in the species *M. furfur* and can also be detected in some of the *M. pachydermatis* isolates.

The pigment-inducing medium (p-agar) is composed of (for 1 liter medium)

| 20 g | agar | e.g. Merck, Darmstadt, Germany |
| 990 ml | aqua dest. | e.g. Pharmacia, Erlangen, Germany |

After autoclaving for 30 min at 1 bar, the following is added:

| 30 ml | Tween 80 | e.g. Sigma, Deishofen, Germany |

At approx. 50° C., the following heat-labile component is added:

| 10 g | L-tryptophan | e.g. Sigma |

The pH value is approximately pH 5.0.

Each 25 ml of the medium are poured into petri dishes with a diameter of 10 cm. A suspension of *M. furfur* CBS 1878 (approx. 5 inoculation loops of a strain previously grown on Dixon's agar) is suspended in 1 ml aq. dest., transferred to the p-agar and spread by tilting the plate. Already after one day of incubation at 32° C. in an incubator, a brown staining of the medium becomes visible which is indicative of pigment synthesis and can be monitored optically. The pigment composition can be determined after extraction and separation via thin layer chromatography.

2. Inhibition of the Pigment Pathway by at Least One Transaminase Inhibitor

Figure 1:
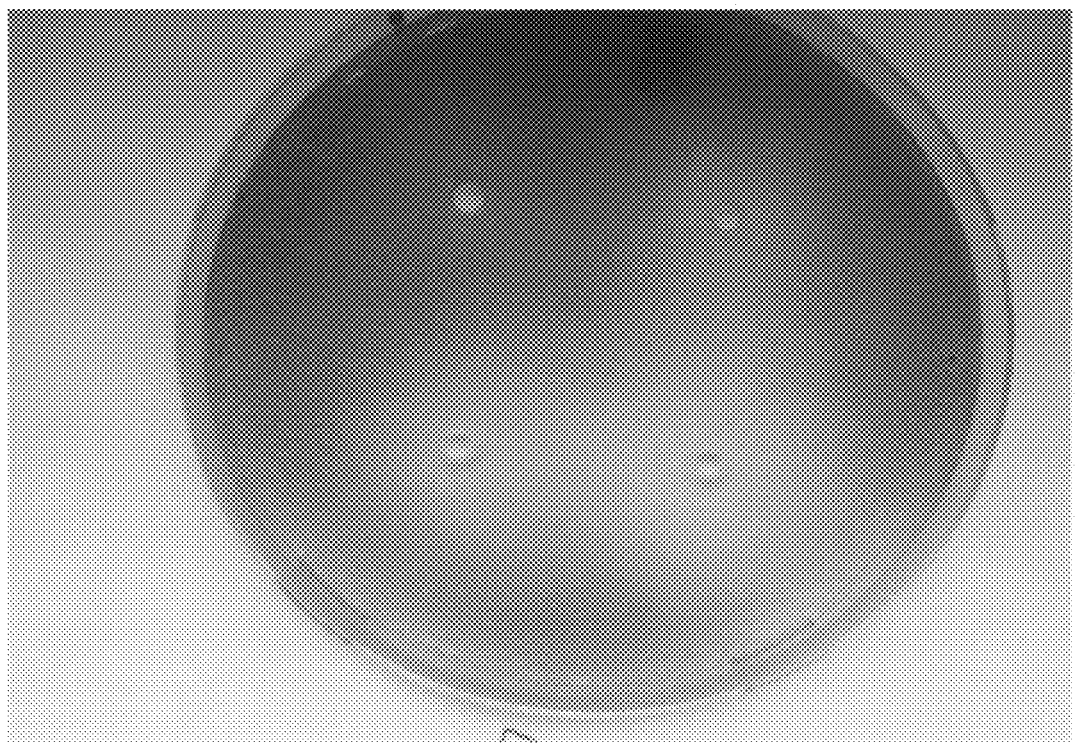
FIG. 1 depicts an agar diffusion assay on a pigment-inducing medium with TRP as the sold nitrogen source.

A complete inhibition of pigment synthesis can for example be demonstrated in agar diffusion assays. For this purpose, *M. furfur* CBS 1878 is spread on the surface of an agar plate with pigment-inducing medium as describe above, subsequently 4 mm-holes are punched into the agar using a sterile punch. Then, each 20 µl of transaminase inhibitor like e.g. aminooxyacetate solution (e.g. Sigma) or cycloserine, e.g. D-cycloserine, DL-cycloserine, L-cycloserine or a derivative thereof such as e.g. terizidone are added in various concentrations to the holes. The result of a 4-days old culture of *M. furfur* CBS 7019 on a pigment-inducing medium with TRP as sole nitrogen source is shown in FIG. 1. The agar diffusion assay is performed with transaminase inhibitor e.g. aminooxyacetate (Sigma) in water, which is adjusted to pH 5 with 1 n NaOH. Concentrations are 0.05 molar top left; 0.1 molar top right; 0.25 molar bottom left, and 0.5 molar bottom right. As demonstrated in FIG. 1, pigment synthesis is abolished in the presence of transaminase inhibitors such as e.g. aminooxyacetate. Furthermore, growth of the fungus is inhibited due to the fact that nitrogen is not available under these specific conditions since transamination is inhibited and other available nitrogen sources are absent.

Figure 2:
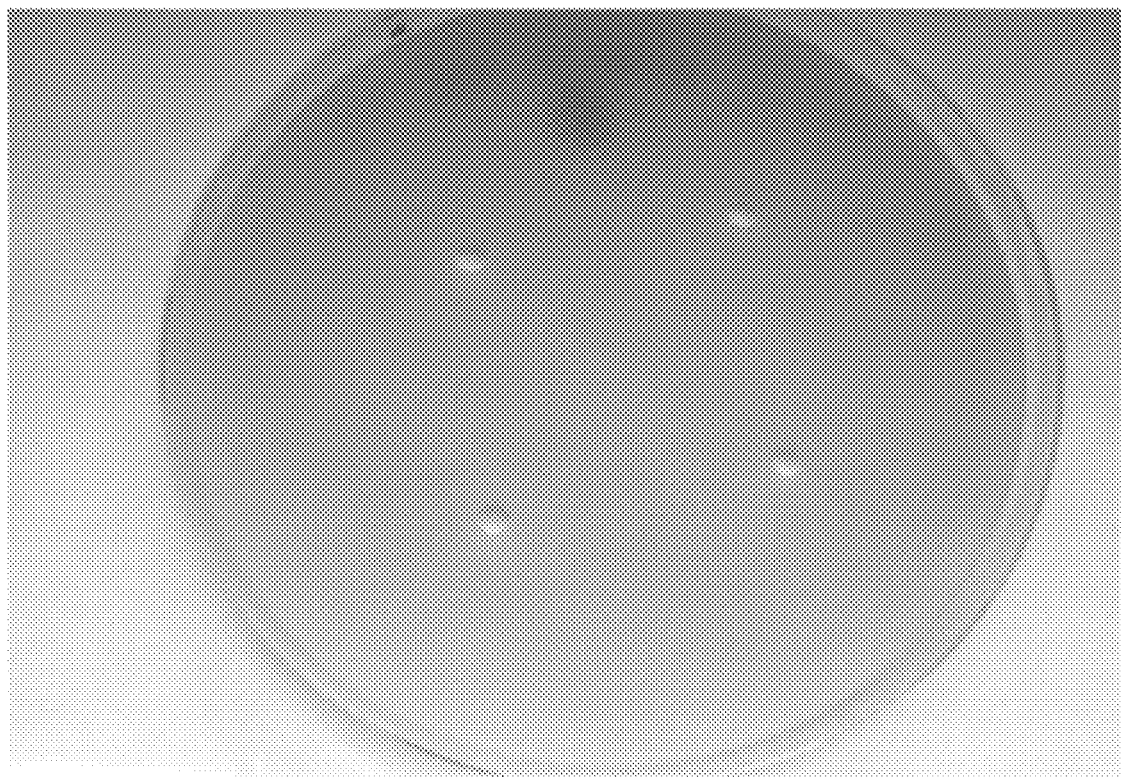
FIG. 2 depicts an agar diffusion assay in which the inhibition of pigment synthesis is due to the specific inhibition of the transaminase.

FIG. 2 demonstrates that the inhibition of pigment synthesis and also the absence of fungal growth is not caused by an antimycotic effect of the at least one transaminase inhibitor, but is due to the specific inhibition of the transaminase. For this purpose, an identical experimental approach as described above is chosen and the fungus is grown on a complete medium Dixon's agar for 4 days. Transaminase inhibitor, e.g. aminooxyacetate solution (e.g. Sigma) or D-cycloserine, DL-cycloserine, L-cycloserine or a derivative thereof such as e.g. terizidone, is added in above mentioned concentrations at the beginning of the experiment. Pigment synthesis is not induced, since several nitrogen sources are available. A specific inhibition of the transamination by aminooxyacetate in concentrations as indicated in FIG. 1 has no effect, since this inhibition can be circumvented.

Furthermore, no toxic effect is detectable. The fungus is growing continuously, also in diffusion zones. Inhibition as demonstrated in FIG. 1 is therefore based on a specific effect.

3. Application in Humans

Transaminase inhibitors such as aminooxyacetate and/or cycloserine, e.g. D-cycloserine, DL-cycloserine, L-cycloserine or one of the derivatives thereof like e.g. terizidone are suitable for an application in humans. A topical application of 5% in unguentum emulsificans aquosum, applied over several days, is well tolerated without side effects. For prophylactic purposes, a 0.05-5% w/w preparation is used, preferably as shaking mixture/suspension cutanea aquosa, aqueous, oily, or alcoholic suspension, emulsion, paste, cream, ointment, spray, lipophilic gel, hydrophilic gel or plaster, shampoo, bath additive or mud, since the entire body should be treated if possible. For prophylaxis, application is performed daily up to several-day intervals. The same applies to the therapeutic use. D-cycloserine is preferably used in aqueous solution, e.g. 0.2 molar, adjusted to pH 7 with e.g. phosphate buffer.

Applied in humans twice a day, this solution results already after three days in a complete healing of lesions without side effects and is very well tolerated.

4. Formulation

The agent of this invention containing at least one transaminase inhibitor for the treatment and prevention of pityriasis is manufactured and formulated in any manner known by experts in this field. Suitable for topical application is for example shaking mixture/suspension cutanea aquosa, aqueous, oily, or alcoholic suspension, emulsion, paste, cream, ointment, spray, lipophilic gel, hydrophilic gel or plaster, also the formulation as medical shampoo, bath additive, or mud is suitable.

For the special manufacturing, the expert knows prior art procedures and adjusts for example oil or moisture content of a cream as well as the pH-value accordingly. Shampoo, solution, gel, cream, and ointment alternatively contain in addition vitamins, UV-protection and fragrances.

Further ingredients used to formulate compositions of this invention comprise e.g. (thixotropic) hydrophilic consistency regulators such as methyl-, hydroxypropyl cellulose, xanthan gum, polyacrylic acids, starch, gelatine, alginates, silicic acid, magnesium aluminum silicate, betonite; (thixotropic) lipophilic consistency regulators like wool wax, glycerol monostearate, cetyl palmitate, cetyl stearyl alcohol, beeswax and hard paraffin; diluents and dispersion agents like water, monohydric alcohols like ethanol, isopropanol or mixtures thereof and polyhydric alcohols like glycols; fatty oils such as soya oil, coconut oil, peanut oil, avocado oil, evening primrose oil, olive oil, cottonseed oil, safflor oil; ethyl oleate, isopropyl myristate and oleyl oleate; silicone oils like dimethicone; and liquid or semi-solid hydrocarbons like vaseline; hard paraffin, ceresine, mineral oils and paraffin oils or low-melting waxes, solubilizing agents; stabilizing agents; buffers, emulsifiers and surfactants like fatty acid esters as for example laureth-4, stareth-2, ceteareth-12, oleth-5, or sorbitan fatty acid esters like e.g. sorbitan monolaurate, -stearate, or polysorbate 20, 40 or 60; polyglyceryl ester, sugar ester or ricinus oil compounds, wetting agents, humectants such as glycerol, propylene glycol, hexylene glycol, butanediol and sorbitol; fatty acids/fatty alcohols; dyes, preservatives like benzoic acid, sorbic acid, phenoxyethanol, benzyl alcohol, parabens and benzalkonium chloride; and antioxidants such as alpha-tocopherol. Ascorbic acid, butylhydroxytoluene, propyl-, dodecyl gallate as well as synergists like citric acid or EDTA; solids such as talcum, titanium(IV) oxide, maize-, rice starch or highly dispersed silicon dioxide; neutralizing agents such as sodium hydroxide, triethanolamine or trometamol; film formers like polyvidone or PVP copolymers and penetration enhancers such as diethylene glycol monoethyl ether.

The agent according to the present invention for the treatment and prophylaxis of pityriasis comprising at least one transaminase inhibitor contains in addition hygroscopic agents such as urea. According to the present invention, also hydrophilic bases may be used, e.g. with carboxymethyl cellulose as gel former. For suspensions and shaking mixtures/suspension cutanea aquosa, mixtures of alcohol/water, of water and ethanol or isopropanol are suitable as dispersing agents.

As basis for oily suspensions and shaking mixtures, in particular fatty oils like olive oil, peanut oil, evening primrose oil or coconut oil are used.

As basis for pastes, birch tar (birch pitch) is particularly suitable. For topical compositions, the content of transaminase inhibitor like e.g. aminooxyacetate or D-cycloserine, DL-cycloserine, L-cycloserine or a derivative thereof like e.g. terizidone is approximately 0.01% to 99%, preferably 0.05% to 50%, particularly preferred is a content of 0.5-5%.

In a preferred embodiment, D-cycloserine (CAS: 68-41-7, 204.2 mg) is used in potassium dihydrogen phosphate/potassium hydrogen phosphate buffer, e.g. as 10 ml solution in which D-cycloserine (CAS: 68-41-7, 204.2 mg) is present in an aqueous potassium dihydrogen phosphate (5 mg)/potassium hydrogen phosphate (167 mg) buffer with a pH-value of 7.

The invention claimed is:

1. A method for treatment of pityriasis versicolor (pityriasis) comprising topically administering to a subject suffering therefrom an effective amount of an agent comprising at least one transaminase inhibitor that suppresses tryptophan-dependent pigment synthesis of *Malassezia* yeasts.

2. The method according to claim 1, characterized in that the transaminase inhibitor specifically inhibits transaminase TAM 1.

3. The method according to claim 1, characterized in that the transaminase inhibitor is aminooxyacetate.

4. The method according to claim 1, characterized in that the transaminase inhibitor is canaline, carboxymethoxylamine, cycloserine, tunicamycin and/or a monoamine oxidase (MAO) inhibitor.

5. The method according to claim 1, characterized in that the transaminase inhibitor is terizidone.

6. The method according to claim 1, characterized in that the transaminase inhibitor is a non-convertible substrate of TAM 1.

7. The method according to claim 1 wherein the agent is formulated in a shaking mixture, suspension cutanea aquosa, aqueous, oily, or alcoholic solution, as emulsion, paste, cream, ointment, spray, lipophilic gel, hydrophilic gel, plaster, shampoo, bath additive or mud.

8. The method according to claim 1, characterized in that the transaminase inhibitor is contained in a concentration of 0.05-5% w/w.

9. The method of claim 6 wherein the non-convertible substrate of TAM 1 is selected from the group consisting of nitrotryptophan, phenelzine, 6-mercaptopurine monohydrate, 6-thioguanine, D-galactosamine hydrochloride, and 2-(hydroxyethyl)urea.

* * * * *